United States Patent [19]

Miller

[11] Patent Number: 5,984,886
[45] Date of Patent: Nov. 16, 1999

[54] SUPPORT BELT

[75] Inventor: James R. Miller, Milton, Mass.

[73] Assignee: Boston Brace International Inc., Avon, Mass.

[*] Notice: This patent is subject to a terminal disclaimer.

[21] Appl. No.: 09/118,774

[22] Filed: Jul. 20, 1998

Related U.S. Application Data

[63] Continuation-in-part of application No. 08/653,277, May 24, 1996, Pat. No. 5,782,782.

[51] Int. Cl.$^6$ .................................. A61F 5/00; A61F 5/02
[52] U.S. Cl. ...................................................... 602/19; 2/44
[58] Field of Search ............................ 602/5–8, 19; 2/44, 2/45; 128/96.1, 99.1, 100.1

[56] References Cited

U.S. PATENT DOCUMENTS

| | | | |
|---|---|---|---|
| 3,434,469 | 3/1969 | Swift | 602/19 |
| 3,871,367 | 3/1975 | Miller | 602/19 |
| 5,363,863 | 11/1994 | Lelli et al. | 602/19 X |
| 5,388,273 | 2/1995 | Sydor et al. | 602/19 X |
| 5,474,523 | 12/1995 | Miller | 602/19 |
| 5,782,782 | 7/1998 | Miller | 602/19 |

*Primary Examiner*—Richard J. Apley
*Assistant Examiner*—Denise Pothier
*Attorney, Agent, or Firm*—Kriegsman & Kriegsman

[57] ABSTRACT

A support belt to be worn around the waist of a person includes an elongated multi-layer strip. The elongated multi-layer strip includes a center portion and a pair of ends. The elongated multi-layer strip is sized and shaped so as to encircle the waist of the person with the center portion positioned against the back of the person and the pair of ends positioned against the front of the person, the pair of ends being releasably fastenable together to secure the support belt around the waist of the person. The center portion of the elongated multi-layer strip is shaped to define an angle of lordosis of approximately 15 degrees in the lumbar spinal region. A pair of inwardly curved sections sized and shaped so as to urge against the iliac crests of the person wearing the support belt are mounted on the multi-layer strip. The multi-layer strip may comprise a layer of rigid plastic and a pair of layers of a soft compressible plastic.

9 Claims, 9 Drawing Sheets

SUPPORT BELT

CROSS-REFERENCE TO RELATED APPLICATIONS

This application is a continuation-in-part of U.S. patent application Ser. No. 08/653,277 filed in the name of James R. Miller on May 24, 1996, now U.S. Pat. No. 5,782,782.

BACKGROUND OF THE INVENTION

The present invention relates generally to support belts and more particularly to a support belt which is designed specifically to conform to the shape and desired angular orientation of the lower back of the wearer.

Back disorders and the pain associated therewith are frequently encountered as a result of lifting, holding, and/or transporting heavy objects. Back disorders and the pain associated therewith are also frequently experienced as a result of placing continuous, high levels of stress on a person's back. Continuous, high levels of stress can occur from, among other things, repeatedly bending over or sitting for a prolonged period of time. Back injuries resulting from heavy lifting and/or repetitive stress generally occur in the curved spinal areas of the lower back, particularly the lumbar or arch spinal region of the back. The lumbar region of the spine corresponds to the five vertebrae which lie directly above the sacrum in the human body.

Support belts, also commonly referred to as lifting belts and weight belts, are well known in the art.

Support belts are commonly employed to reduce the likelihood of back injuries resulting from repetitive stress and heavy lifting. Support belts are worn to support the lower back of the wearer. Specifically, support belts are often worn to support the lumbar region of the spine of the wearer as well as to support the muscles surrounding the lumbar spinal region, thereby limiting muscle strains and pulls.

One well known type of support belt comprises a strip of flat, stiff, rigid leather, about ¼ inch to ½ inch thick, which is wide in the back with a gradual taper toward a narrower front. To secure the belt around the waist of the wearer, the belt commonly includes a buckle having a pin on one side of the strap and a plurality of holes on the other side of the strap.

It has been found that support belts of the type described above do not adequately provide uniform support to the curved spinal areas of the back, particularly the lumbar or arch region of the back. Specifically, the inherent inflexibility of the strip of leather prevents the belt from providing uniform surface contact with the curved lumbar area of the back. As a result, portions of the lumbar spinal region of the back of the wearer are inadequately supported and therefore susceptible to injury.

In addition, such belts do not position the lumbar region of the spine at the ideal angle of lordosis (i.e. approximately 15 degrees), the angle of lordosis referring to the forward curvature of the lumbar region of the spine which produces the arch in the back of a person. To the contrary, because such belts are flat, they will have a tendency to position the lumbar spinal region at an angle of about 0 degrees, which can potentially lead to spinal malalignment and associated injuries.

It has also been found that such belts tend to be uncomfortable for most wearers. Specifically, because such belts do not accurately imitate the exact shape of the back of the wearer, the belts will tend to pinch the pelvic wings, or iliac crests of the wearer when the wearer bends over or moves.

Another well known type of support belt comprises a strip of a flexible, elastic type material which is secured around the waist of the wearer.

Unfortunately, such flexible belts provide less support than the rigid belts and are therefore not suitable for activities which require heavy lifting. Moreover, due to the lack of support, flexible belts do not adequately promote and/or protect the proper spinal curvature of the wearer, particularly in the lumbar region.

In U.S. Pat. No. 5,437,615 to Pekar et al there is described a support belt which is intended to encircle a wearer's waist. The belt, which is made of a stiff material such as leather, has an on-board inflation pump and may be used for weight lifting. The belt includes a bladder defined by a single chamber having inflation and deflation mechanisms which allow the wearer to selectively adjust the amount of air in the bladder. The bladder has an oblong portion which is positioned on the belt so that when the belt is worn, the oblong portion is positioned adjacent to the wearer's lower back for support. An elongated portion of the bladder extending through the aperture of the belt is integrally formed with inflation and deflation mechanisms on the other side of the belt. In the preferred embodiment, the inflation mechanism comprises a pump and a one-way valve and the deflation mechanism comprises an exhaust valve.

In U.S. Pat. No. 5,399,150 to Saunders there is disclosed a lumbosacral back support system with interchangeable and positionally adjustable lumbosacral orthopedic support members for supporting the spine of a user during physical activity, specifically for athletes and industrial workers. A back support band is provided with a first releasable attachment mechanism. A lumbosacral support member with a second releasable attachment mechanism is provided for engagement with the first releasable attachment mechanism. The first and second releasable attachment mechanisms are arranged for attaching a lumbosacral support member to the back support band at a variety of positions relative to the spine of the user. The releasable attachment mechanism provides the user with the option to substitute different lumbosacral support members on the back support band. Additionally, the back support band may be releasably attached to a compression-type short to further secure the lumbosacral back support system to the user.

In U.S. Pat. No. 5,399,151 to Smith there is disclosed a lifting belt containing basically three elements, namely, an underlying wrap assembly with expandable back panel and overlapping closure ends, suspenders with four adjustable ends to secure to the underlying wrap assembly at varying positions in front and at two positions varying vertically in the rear, and expandable side pull portions which have a pair of elastic band portions and removably secured end tabs. The expandable side pulls are normally applied by snugly securing the side pulls to the underlying wrap assembly prior to lifting.

In U.S. Pat. No. 5,388,274 to Glover et al there is disclosed an improved orthopedic device for human wear comprising of a flexible belt with free ends thereof joined by a hook and loop fastener to position the belt on the wearer, and wherein the flexible belt is provided with a pad to be positioned against the lumbar and sacral regions of the wearer and with vertical stiffeners for the flexible belt. A static support is fixedly attached to the flexible belt and completely encircles the wearer. The static support is bi-level with one level encircling the wearer, extending around the flexible belt, and attached thereto adjacent the pad, and is provided with adjustable length belt buckle ends for cinching the one level about the user with varying degrees of tension. A second level is V-shaped and is attached to the elastic belt adjacent to the pad to dispense the support to the sacral regions when additional support is desired and the buckled clasp and first level tightened.

In U.S. Pat. No. 5,474,523 to J. J. Miller there is disclosed a hard body brace for treating scoliosis in a patient while preventing hypokyphosis in the patient's thoracic spine. As preferably envisioned by the present invention, the hard body brace may be fabricated by the manufacturer as an unfinished brace and may then be finished on site by an orthotist to meet the exact size and shape of the intended wearer. In a preferred embodiment, the unfinished hard body brace comprises a shell shaped to surround the torso of a person in such a way as to correct scoliosis, the shell having an outer layer of hard plastic material and an inner layer of compressible plastic material bonded to the outer layer. The shell is preferably made from a single section and has a vertically extending split portion. To prevent hypokyphosis, the shell is shaped to define a kyphotic angle in the thoracic spine of approximately 20 to 25 degrees. The shell may additionally be shaped to define a lordotic angle in the lumbar spine of approximately 15 degrees to make the brace more comfortable to the wearer.

In U.S. Pat. No. 3,871,367 to M. E. Miller there is disclosed a pelvic girdle comprising an outer layer of a hard substantially rigid plastic material and an inner layer of soft compressible plastic material bonded to the outer layer, the girdle being shaped to engage a person's pelvis and including an anterior and a vertically split posterior portion, the girdle having an upper anterior portion separated laterally from the remainder of the girdle and curving outwardly thereof, and connecting upper side portions on the girdle connecting the anterior and posterior portions thereof and including inwardly curved sections in both layers of the girdle for engaging the iliac crests of the wearer and which sections have appreciably thicker compressible inner layers thereon.

SUMMARY OF THE INVENTION

It is an object of the present invention to provide a new and improved support belt.

It is yet another object of the present invention to provide a support belt as described above which comprises a strip of material.

It is still another object of the present invention to provide a support belt as described above which positions the spine of the wearer at the proper angle of lordosis.

It is yet another object of the present invention to provide a support belt as described above which closely imitates the shape of the lower back of the wearer.

It is still another object of the present invention to provide a support belt as described above which provides uniform support to the curved spinal areas of the back of the wearer.

It is yet another object of the present invention to provide a support belt as described above which is comfortable.

Accordingly, there is provided a support belt to be worn around the waist of a person.

In one embodiment of the invention, the support belt comprises an elongated strip of rigid material having a center portion and a pair of ends, said elongated strip of rigid material being sized and shaped so as to encircle the waist of the person with the center portion positioned against the back of the person and the pair of ends positioned against the front of the person, and wherein said elongated strip of rigid material is shaped to define an angle of lordosis of approximately 15 degrees in the lumbar spinal region.

In other embodiments of the invention the support belt comprises an elongated multi-layered strip having a center portion and a pair of ends, said elongated multi-layer strip having a center portion and a pair of ends, said elongated multi-layer strip being sized and shaped so as to encircle the waist of the person with the center portion positioned against the lumbar spinal region of the back of the person, the center portion of said elongated multi-layered strip being shaped to define an angle of lordosis of approximately 15 degrees, said elongated multi-layered strip comprising at least one layer of soft compressible plastic material and at least one layer of rigid plastic material.

According to one feature of the invention the support belt includes means for engaging the iliac crests of the person wearing the support belt.

Additional objects, as well as features and advantages, of the present invention will be set forth in part in the description which follows, and in part will be obvious from the description or may be learned by practice of the invention. In the description, reference is made to the accompanying drawings which form a part thereof and in which is shown by way of illustration specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is therefore, not to be taken in a limiting sense, and the scope of the present invention is best defined by the appended claims.

BRIEF DESCRIPTION OF THE DRAWINGS

In the drawings wherein like reference numerals represent like parts.

DETAILED DESCRIPTION OF PREFERRED EMBODIMENTS

The present invention is directed to a support belt which closely imitates the shape of the lower back of the wearer and which also positions the spine of the wearer at the proper angle of lordosis in the lumbar spinal region, the angle of lordosis being approximately 15 degrees.

Figure 1:
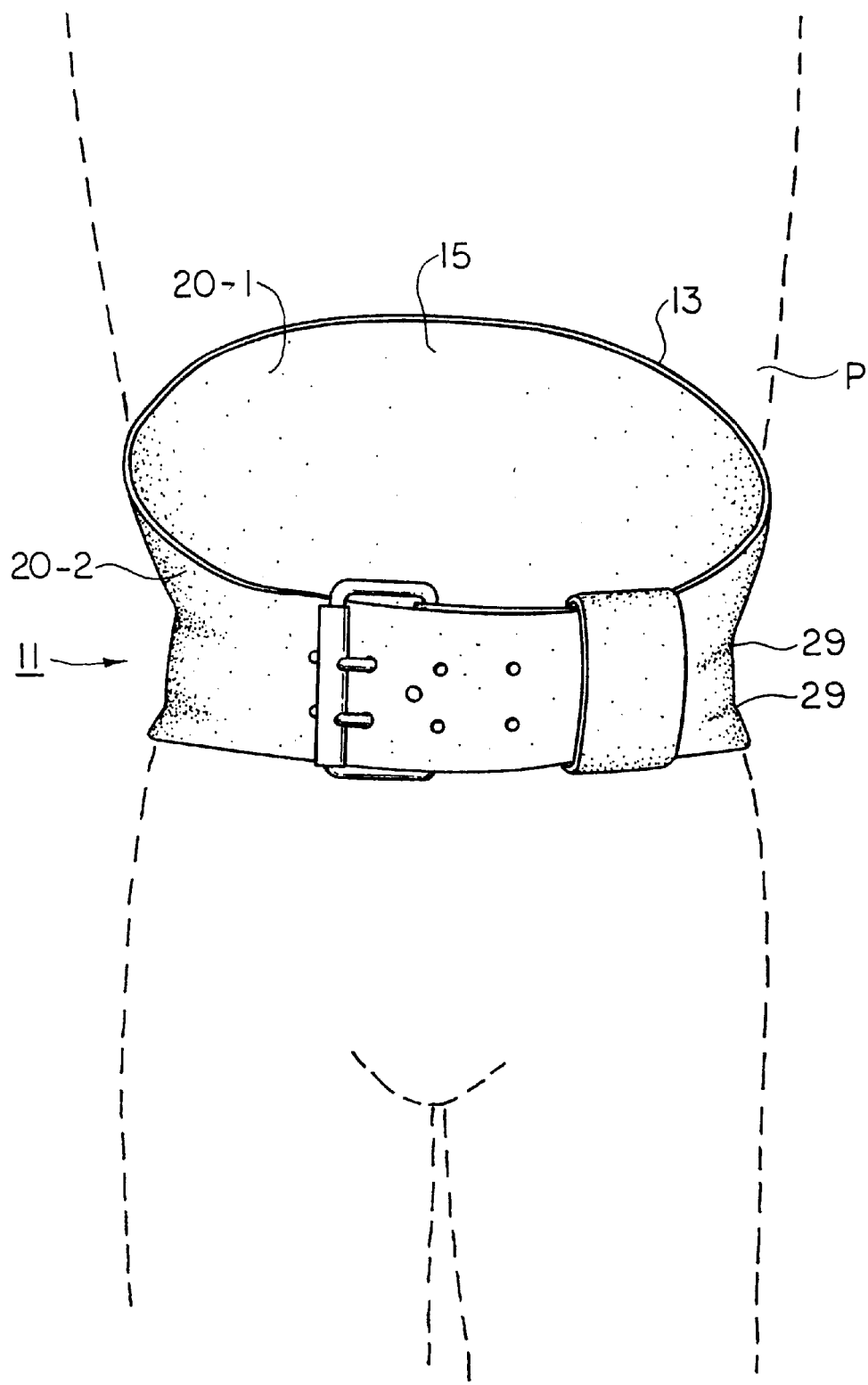
FIG. 1 is a front view of one embodiment a support belt constructed according to this invention, said support belt being shown positioned around the waist of a person.
Figure 2:
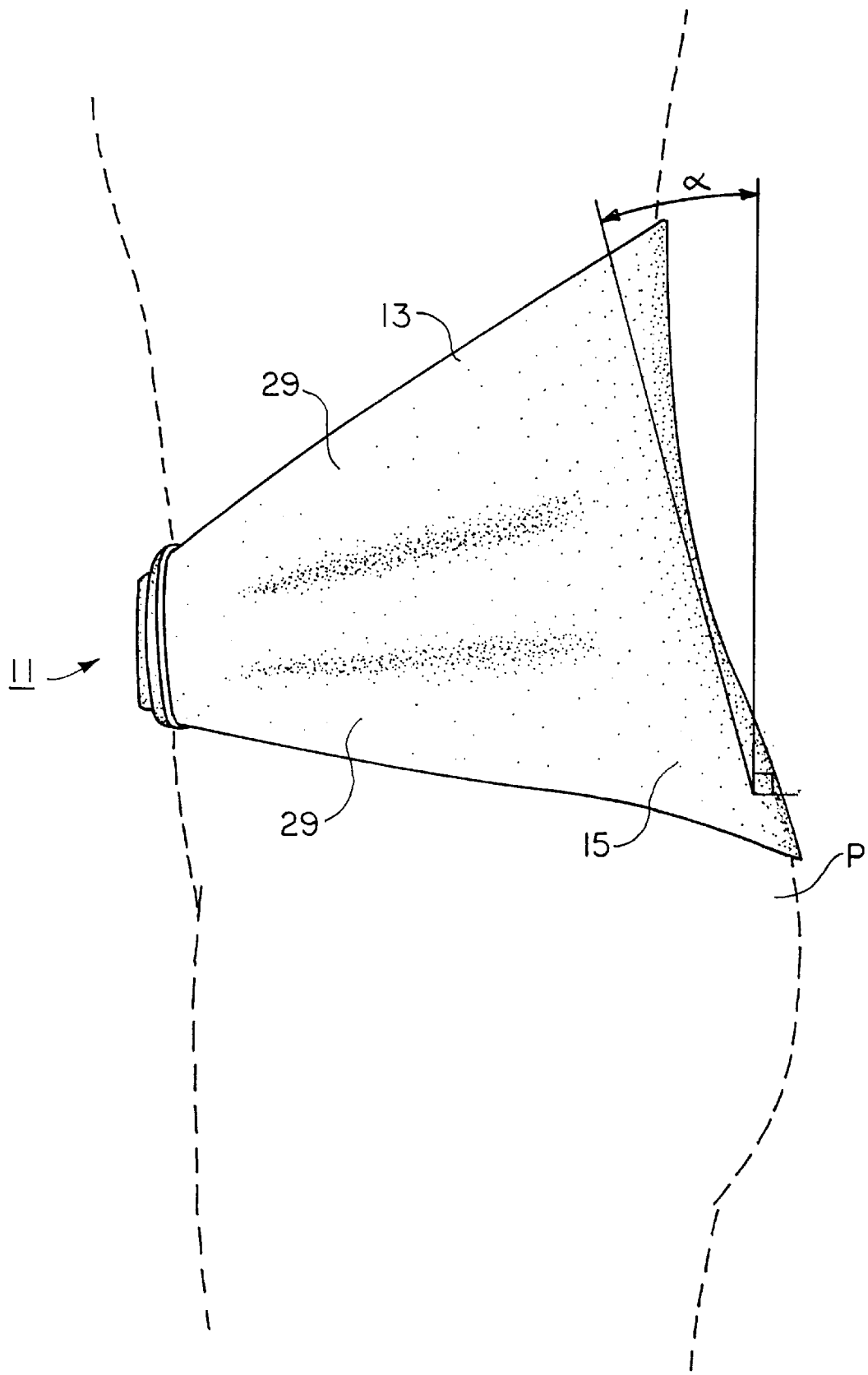
FIG. 2 is a side view of the support belt of FIG. 1, the support belt being shown positioned around the waist of a person.
Figure 3:
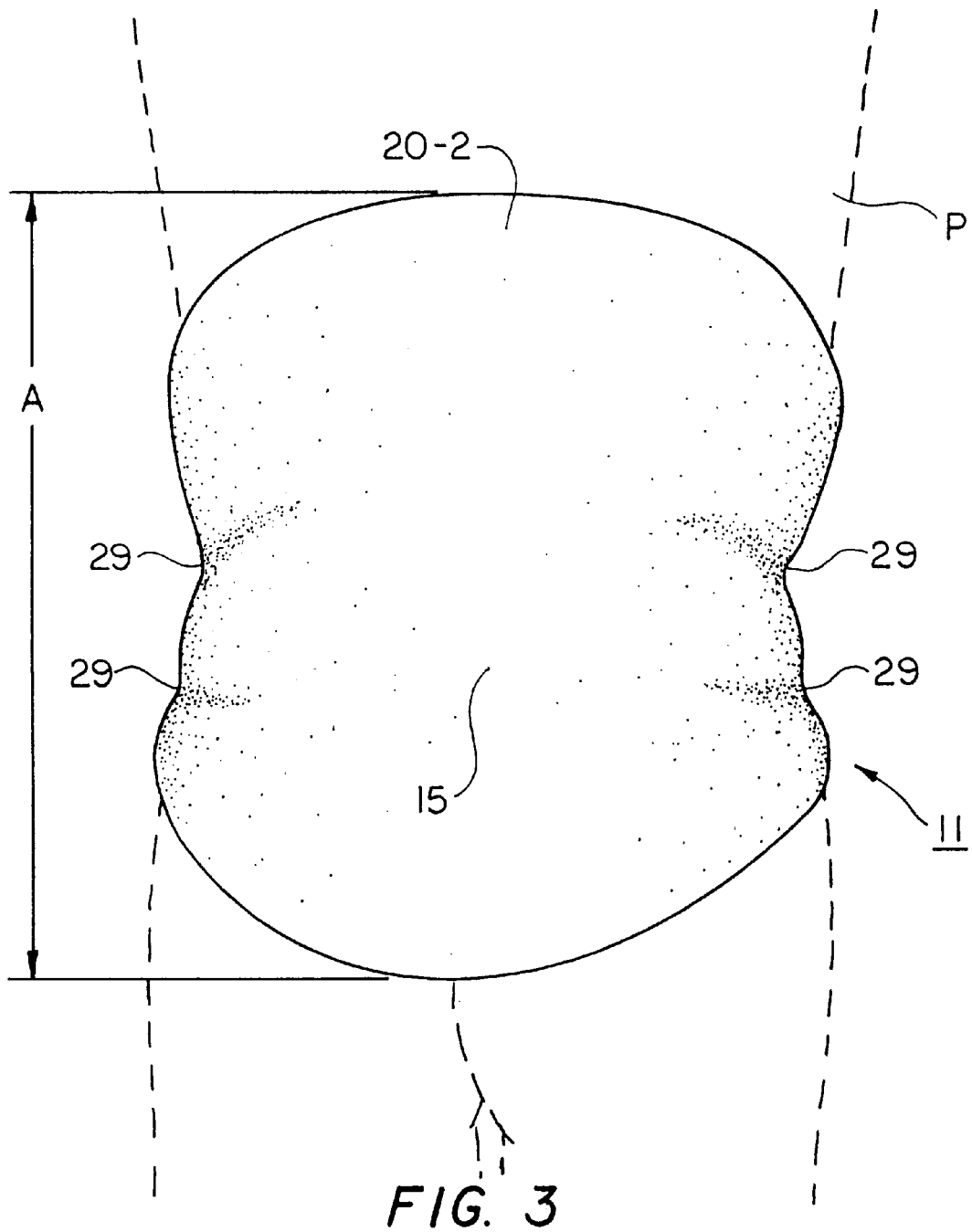
FIG. 3 is a rear view of the support belt of FIG. 1, the support belt being shown positioned around the waist of a person.
Figure 4:
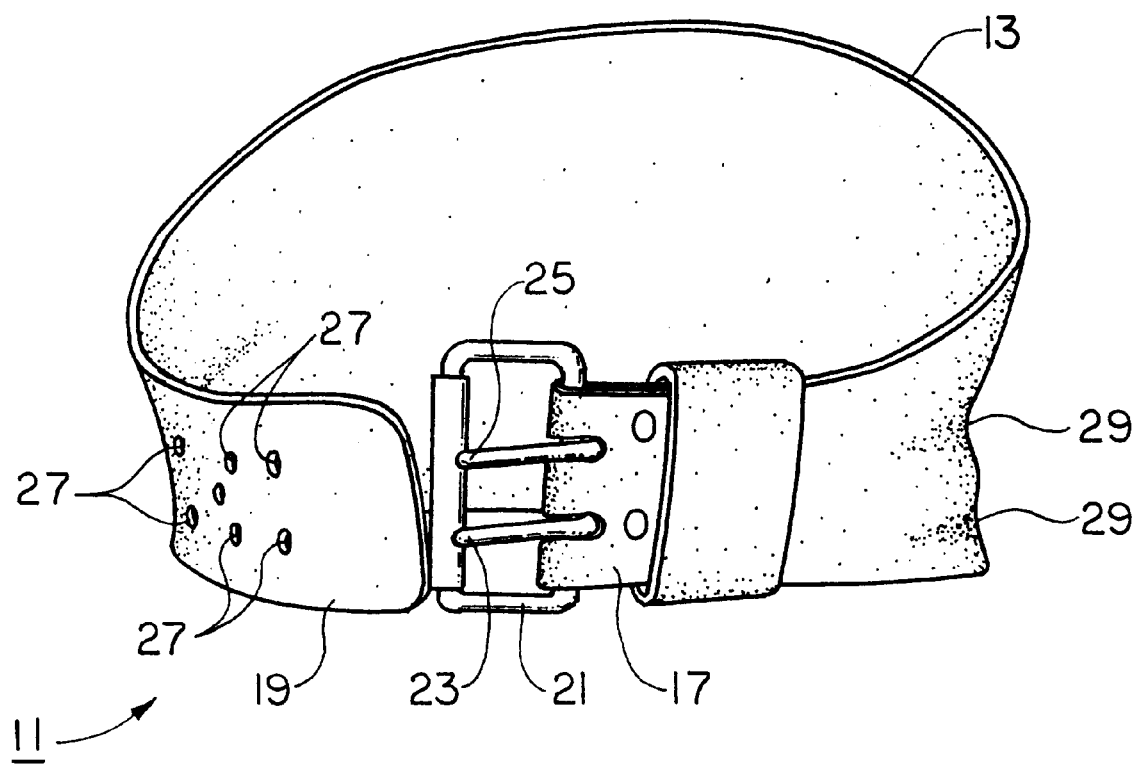
FIG. 4 is a front view of the support belt of FIG. 1, the support belt being shown unbuckled and partially open.

Referring to the drawings, there are shown in FIGS. 1–5, one embodiment of a support belt constructed according to this invention, the support belt being identified by reference numeral 11. In FIGS. 1–3, support belt 11 is shown positioned around the waist of a person P.

Support belt 11 includes an elongated strip of rigid, i.e. non-flexible, material 13. Elongated strip of rigid material 13 is constructed of a low density material such as polyethylene to provide firm support to the back of person P; however, the rigid material could be materials other than polyethylene or other types of plastics. Although support belt 11 is shown as comprising a single, elongated strip of rigid material, support belt 11 could be similarly constructed of a plurality of layers, one of the layers being of a rigid material. Support belt 11 could also be constructed to include a liner which can be removably attached by any suitable means to the inner surface of the belt, the liner serving to limit irritation against the skin of the wearer. Furthermore, support belt 11 could be constructed using one or more soft plastic layers whose shape is held in place by one or more rigid stays on the inside, outside, or in between the soft plastic layers. A support belt identified by reference numeral 11-1 and comprising a layer 11-2 of soft plastic material whose shape is held in place by a plurality of rigid stays 11-3 attached by an adhesive (not shown) on the outside of layer 11-2 is shown in FIGS. 5A and 5B.

Elongated strip of rigid material 13 comprises a center portion 15, first end 17, a second end 19, an inner surface 20-1 and an outer surface 20-2. Center portion 15 and ends 17 and 19 are integrally formed together as a single unit, such as through molding. Elongated strip of rigid material 13 is sized and shaped so as to encircle the waist of person P with center portion 15 positioned against the back of person P and ends 17 and 19 positioned against the front of person P. Center portion 15 has a width A which is wide enough so as to conform to the lower back of person P, particularly the lumbar region. Center portion 15 gradually tapers inward towards narrower front ends 17 and 19.

Belt 11 further includes a buckle 21 and a pair of pins 23 and 25, buckle 21 and pins 23 and 25 being pivotally mounted onto the free end of first end 17. Second end 19 includes a plurality of holes 27. Buckle 21, pins 23 and 25 and holes 27 together serve to releasably fasten ends 17 and 19 together, thereby securing belt 11 around the waist of person P. Specifically, after belt 11 has been properly positioned around the waist of person P, second end 19 is fed through buckle 21 to tighten belt 11 around the waist of person P. Once belt 11 has been sufficiently tightened, pins 23 and 25 engage with plurality of holes 27 to secure belt 11 in position around the waist of person P.

Center portion 15 of belt 11 is sized and shaped so as to conform to the lower back of person P. Referring to FIG. 2, center portion 15 is shaped to define an angle of lordosis α of approximately 15 degrees in the lumbar spinal region, this angle being the appropriate forward curvature in this region. Center portion 15 is shaped to define the desired angle of lordosis in order to properly position the lumbar spinal region of person P at the proper curvature and to provide uniform support to the entire arched lumbar spinal region of person P.

Referring now to FIG. 3, elongated strip of material 13 further includes a pair of inwardly curved sections 29, one on each side of belt 11. Inwardly curved sections 29 are sized and shaped so as to urge against the iliac crests of person P, thereby improving the conformity of belt 11 to the shape of person P and improving comfort.

It should be noted that belt 11 may either be preformed into standard sizes, such as small, medium and large (such as for males, females and children) or belt 11 may be casted and formed directly from the body of the patient.

Figure 5:
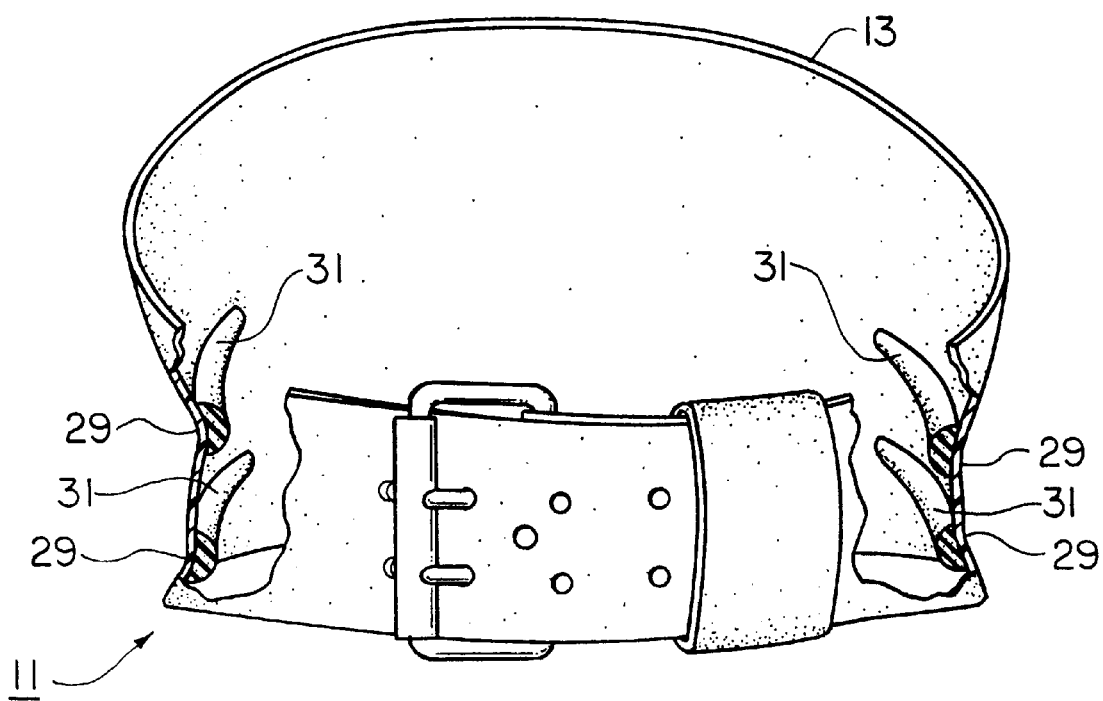
FIG. 5 is a front view partly broken away in section of the support belt shown in FIG. 1.
Figure 6:
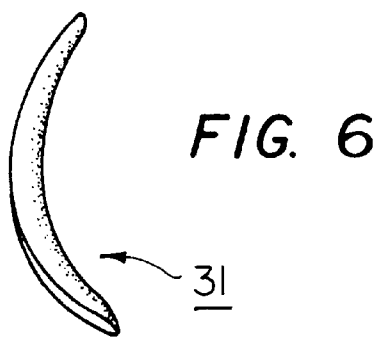
FIG. 6 is a perspective view of one of the iliac crest pads shown in FIG. 5.
Figure 5A:
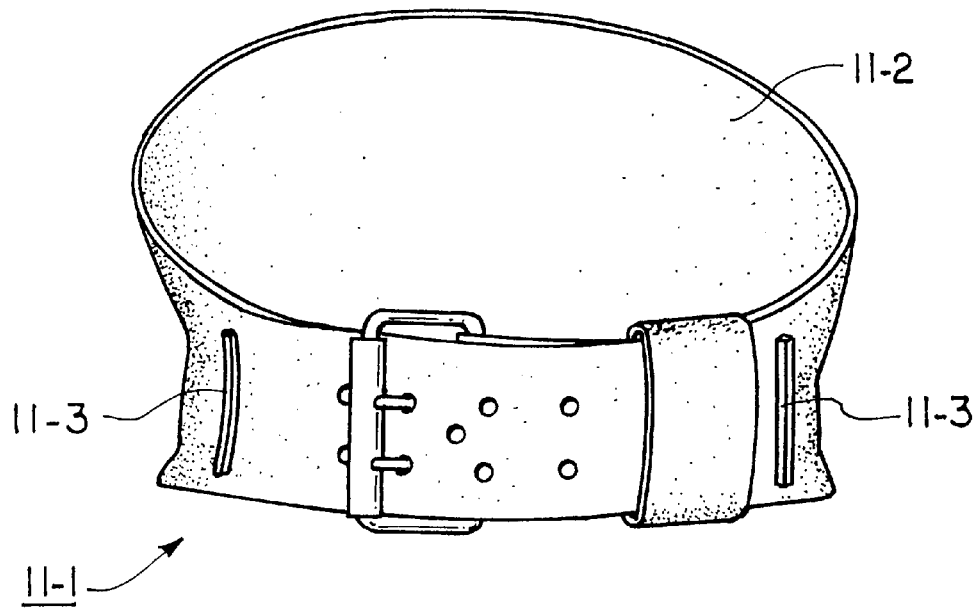
FIGS. 5A and 5B are front and rear views, respectively, of another embodiment of the invention.
Figure 5B:
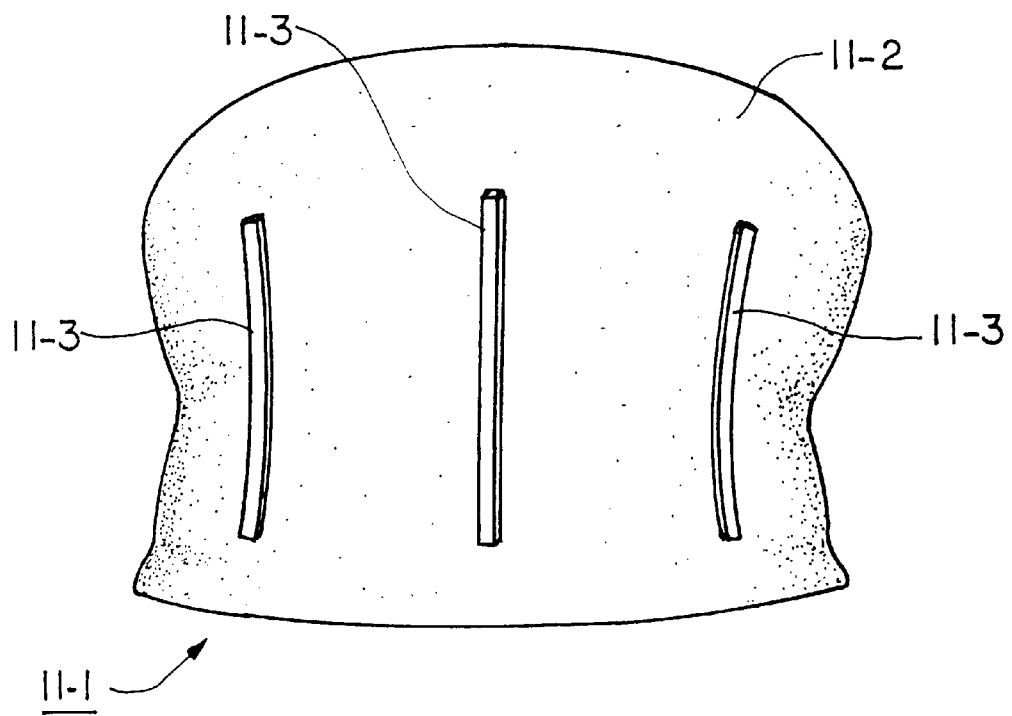

As can be seen in FIG. 5, a pair of iliac crest pads 31 are attached to inner surface 20-1 of belt 11 one at each inwardly curved section 29 by an attachment means (not shown) such as hook and pile fasteners, adhesive, or other suitable means. Iliac crest pads 31 serve to improve the conformity of belt to the exact dimensions of the body of the wearer. Iliac crest pads 31 may be made, for example of a soft compressible plastic material, such as 6 lb. polyethylene foam.

Figure 7:
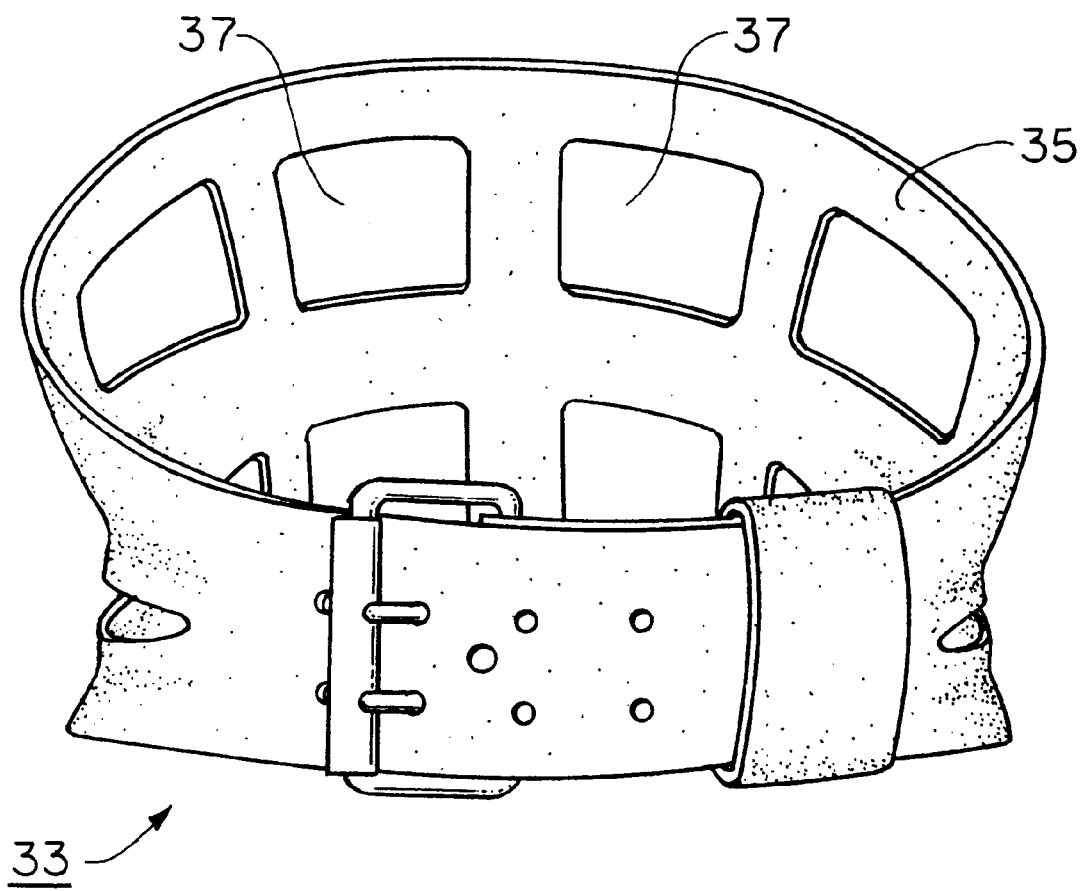
FIG. 7 is a front view of a second embodiment of a support belt constructed according to this inventions.

Referring to FIG. 7, there is shown a second embodiment of a support belt constructed according to this invention, the support belt being identified by reference numeral 33. Support belt 33 is identical in construction to belt 11 except that support belt 33 comprises a frame 35 having one or more openings 37 rather than a solid sheet of material. As can be appreciated, frame 35 could be further attached to pieces of rigid plastic by rivets for additional support (not shown).

Figure 8:
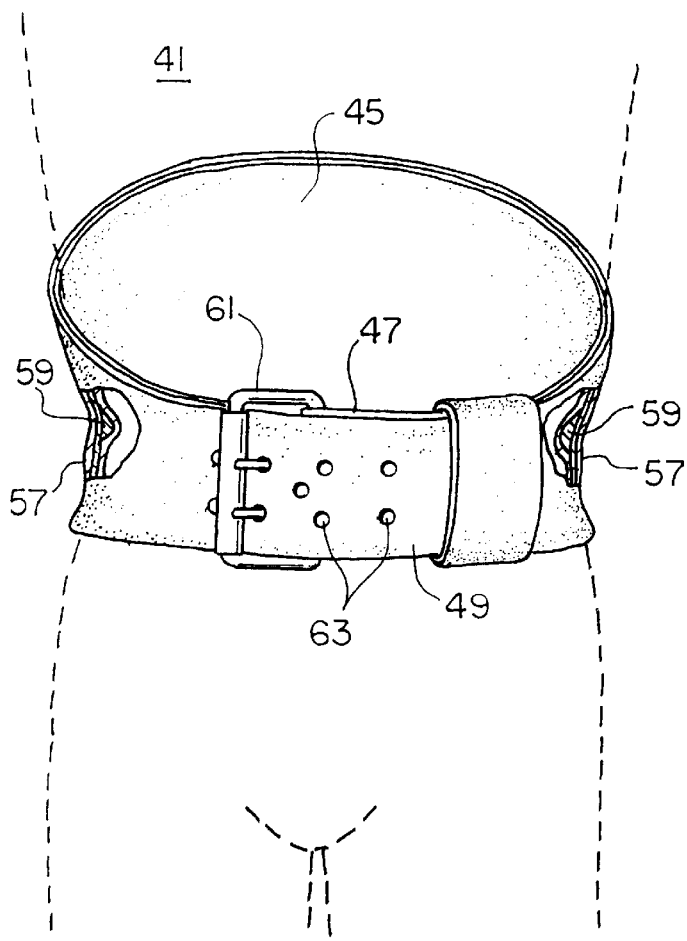
FIG. 8 is a front view of another embodiment of a support belt constructed according to this invention.
Figure 10:
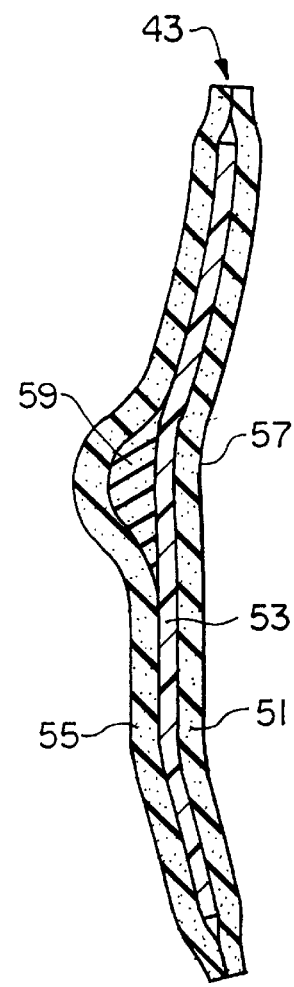
FIG. 10 is an enlarged section view taken along lines 10—10 in FIG. 9.
Figure 9:
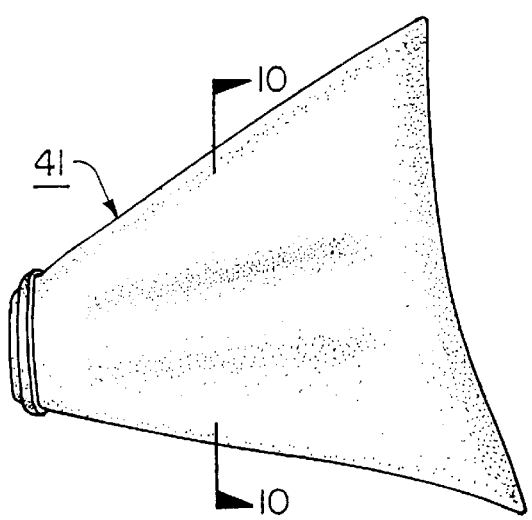
FIG. 9 is a side view of the support belt shown in FIG. 8.

Referring now to FIGS. 8 through 10, there is shown a third embodiment of a support belt constructed according to this invention, the support belt being identified by reference numeral 41.

Support belt 41 includes a multi-layer strip 43 sized and shaped to encircle the waist of a person and includes a center portion 45, a first end 47 and a second end 49. Center portion 45 is sized and shaped to conform to the lower back of a person and as such is shaped to define an angle of lordoses α of approximately 15 degrees in the lumbar spinal region.

Multi-layer strip 43 comprises an outer layer 51 of a soft compressible plastic material, such as polyethylene foam, a middle layer 53 of a hard plastic, such as a sheet of polyethylene and an inner layer 55 of a soft compressible plastic material, such as polyethylene foam. Outer layer 51 may be, for example, 12 lb. polyethylene foam, about ⅛ of an inch thick, middle layer 53 may be about ⅛ of an inch thick, and inner layer 55 may be, for example 6 lb. polyethylene foam about 3/16 of an inch thick. Middle layer 53 is bonded by any suitable means to inner layer 55 and outer layer 51 is bonded by any suitable means to middle layer 53. Middle layer 53 holds the shape of belt 41 while inner layer 53 limits irritation against the skin of the wearer.

Multi-layer strip 43 further includes a pair of inwardly curved sections 57, one on each side of belt 41 for engaging the iliac crests of the person wearing support belt 41. A pair of iliac crest pads 59, identical to iliac crest pads 31 are bonded in place at inwardly curved section 57, between inner layer 55 and middle layer 53.

Belt 41 further includes a buckle and pins 61 on first end 47 and holes 63 on second end 49.

Figure 11:
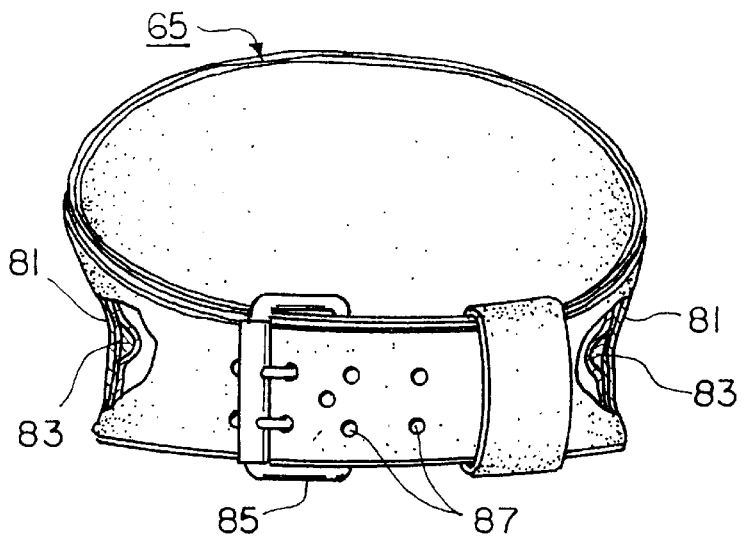
FIG. 11 is a front view of a another embodiment constructed according to this invention.
Figure 12:
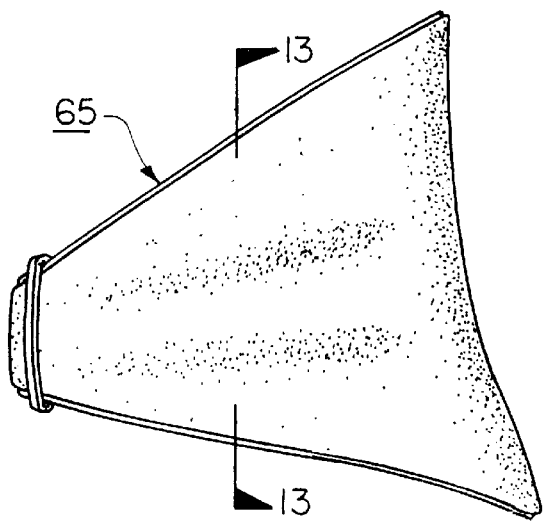
FIG. 12 is a side view of the support belt shown in FIG. 11.
Figure 13:
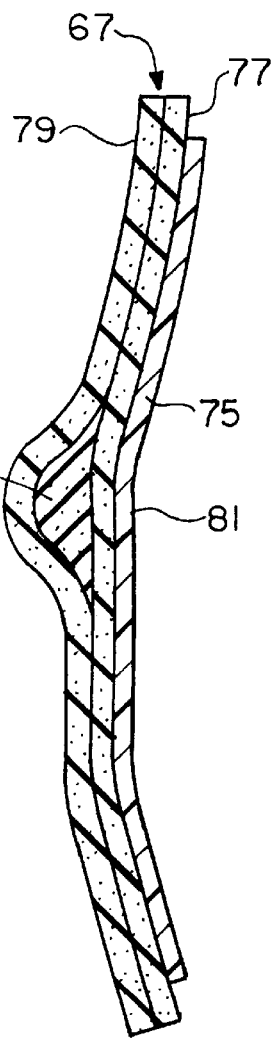
FIG. 13 is an enlarged section view taken along lines 13 in FIG. 12.

In FIGS. 11–13 is shown another embodiment of a support belt according to this invention, the support belt being identified by reference numeral 65.

Support belt 65 includes a multi-layer strip 67 identical in size and shape to trip 43. Strip 47 includes a center portion 69, a first end 71 and a second end 73.

Strip 67 includes an outer layer 75 of a hard plastic such as polyethylene, a middle layer 77 of a soft compressible plastic material, such as polyethylene foam and an inner layer 79 of a soft compressible plastic material such as polyethylene foam. Outer layer 75 may be ⅛ of an inch thick, middle layer 77 may be 12 lb. polyethylene foam, about 3.16 of an inch thick. Outer layer 75 holds the shape of bell 65 while layers 77 and 79 limit irritation on the skin of the wearer.

Strip 67 also includes inwardly curved sections 81, one on each side of belt 65 to engage the iliac crests of the wearer and iliac crest pads 83 at the inwardly curved sections 81, between inner layer 79 and middle layer 77.

Finally, belt 65 includes a buckle and pins 85 at first end 71 and holes 87 at second end 73.

The embodiments of the present invention described above are intended to be merely exemplary and those skilled in the art shall be able to make numerous variations and modifications to it without departing from the spirit of the present invention. All such variations and modifications are intended to be within the scope of the present invention as defined by the appended claims.

What is claimed is:

1. A support belt to be worn around the waist of a person, said support belt comprising an elongated multi-layered strip having a center portion and a pair of ends, said elongated multi-layer strip being sized and shaped so as to encircle the waist of the person with the center portion positioned against the lumbar spinal region of the back of the person, the center portion of said elongated multi-layered strip being shaped to define an angle of lordosis of approximately 15 degrees, said elongated multi-layered strip comprising an inner layer of soft compressible plastic material, an outer layer of soft compressible plastic material and a middle layer of rigid plastic material, said middle layer being disposed between said outer layer and said inner layer.

2. A support belt to be worn around the waist of a person, said support belt comprising an elongated multi-layered strip having a center portion and a pair of ends, said elongated multi-layer strip being sized and shaped so as to encircle the waist of the person with the center portion positioned against the lumbar spinal region of the back of the person, the center portion of said elongated multi-layered strip being shaped to define an angle of lordosis of approximately 15 degrees, said elongated multi-layered strip comprising an inner layer of soft compressible plastic material, an outer layer of rigid plastic material and a middle layer of soft compressible plastic material, said middle layer being disposed between said outer layer and said inner layer.

3. A support belt to be worn around the waist of a person, said support belt comprising an elongated multi-layered strip having a center portion and a pair of ends, said elongated multi-layer strip being sized and shaped so as to encircle the waist of the person with the center portion positioned against the lumbar spinal region of the back of the person, the center portion of said elongated multi-layered strip being shaped to define an angle of lordosis of approximately 15 degrees, said elongated multi-layered strip comprising an inner layer of soft compressible plastic material and an outer layer of rigid plastic material.

4. A support belt to be worn around the waist of a person, said support belt comprising an elongated multi-layered strip having a center portion and a pair of ends, said elongated multi-layer strip being sized and shaped so as to encircle the waist of the person with the center portion positioned against the lumbar spinal region of the back of the person, the center portion of said elongated multi-layered strip being shaped to define an angle of lordosis of approximately 15 degrees, said elongated multi-layered strip comprising at least one layer of soft compressible plastic material and at least one layer of rigid plastic material.

5. The support belt of claim 4 wherein said elongated strip includes a pair of inwardly curved sections sized and shaped to urge against the iliac crests of a person.

6. The support belt of claim 5 and further including a pair of iliac crest pads, one attached to each inwardly curved section to improve the conformity of the belt to the wearer.

7. A support belt to be worn around the waist of a person, said support belt comprising an elongated strip of soft compressible material having a center portion and a pair of ends, said elongated strip of soft compressible material being sized and shaped so as to encircle the waist of the person with the center portion positioned against the lumbar spinal region of the back of the person, the center portion of said elongated strip of soft compressible material being shaped to define an angle of lordosis of approximately 15 degrees, and on said elongated strip of soft compressible material for holding the shape of said elongated strip of soft compressible material.

8. The support belt of claim 7 wherein said elongates strip includes a pair of inwardly curved sections sized and shaped to urge against the iliac crests of a person.

9. The support belt of claim 8 and further including a pair of iliac crest pads, one attached to each inwardly curved section to improve the conformity of the belt to the wearer.

* * * * *